United States Patent [19]

Timonen et al.

[11] Patent Number: 5,543,162
[45] Date of Patent: Aug. 6, 1996

[54] POLYMERIC CAPSULES, METHOD OF MAKING THE SAME, AND FOODSTUFFS CONTAINING THE SAME

[75] Inventors: Maritta Timonen, Helsinki, Finland; Chokyun Rha, Boston, Mass.

[73] Assignee: Alko Group Ltd., Helsinki, Finland

[21] Appl. No.: 344,107

[22] Filed: Nov. 23, 1994

Related U.S. Application Data

[60] Division of Ser. No. 825,035, Jan. 24, 1992, abandoned, and a continuation-in-part of Ser. No. 743,152, Aug. 9, 1991, Pat. No. 5,366,755, Ser. No. 730,029, Jul. 12, 1991, abandoned, Ser. No. 567,045, Aug. 10, 1990, abandoned, Ser. No. 565,346, Aug. 10, 1990, abandoned, Ser. No. 464,291, Jan. 12, 1990, abandoned, Ser. No. 370,629, Jun. 23, 1989, abandoned, and Ser. No. 309,387, Feb. 10, 1989, abandoned.

[51] Int. Cl.$^6$ ........................................... A23L 1/00
[52] U.S. Cl. .................... 426/89; 127/37; 426/48; 426/658; 426/801; 536/56; 536/84
[58] Field of Search ..................... 426/549, 49, 89, 426/52, 48, 531, 601, 603, 658, 659, 660, 801, 103, 573, 574, 575, 576, 577, 578; 536/56, 84, 85, 86, 88, 89; 127/37

[56] References Cited

U.S. PATENT DOCUMENTS

| | | | |
|---|---|---|---|
| 3,397,198 | 8/1968 | Greidinger et al. | 536/57 |
| 4,048,433 | 9/1977 | Burns et al. | 536/99 |
| 4,143,163 | 3/1979 | Hutchinson et al. | 426/96 |
| 4,230,687 | 10/1980 | Sair et al. | 424/22 |
| 4,281,063 | 7/1981 | Tsao et al. | 435/99 |
| 4,314,854 | 2/1982 | Takagi | 127/37 |
| 4,316,982 | 2/1982 | Holst et al. | 536/88 |
| 4,427,584 | 1/1984 | LeGrand et al. | 127/37 X |
| 4,470,851 | 9/1984 | Paszner et al. | 127/37 |
| 4,664,717 | 5/1987 | Young | 127/37 |
| 4,681,935 | 7/1987 | Forss et al. | 536/56 |

FOREIGN PATENT DOCUMENTS

| | | |
|---|---|---|
| 0149258 | 7/1985 | European Pat. Off. |
| 277111 | 9/1927 | United Kingdom |
| 953944 | 4/1964 | United Kingdom |

*Primary Examiner*—Leslie Wong

[57] ABSTRACT

An insoluble polymeric capsule comprising at least two polymeric components, wherein one of said components is a hydrophilic colloid, and another of said components comprises a degradation product of a cellulose derivative, the degradation product comprising a mixture of oligomers, a majority of said oligomers having a degree of polymerization such that the oligomers conform to a rod-like configuration.

32 Claims, 8 Drawing Sheets

POLYMERIC CAPSULES, METHOD OF MAKING THE SAME, AND FOODSTUFFS CONTAINING THE SAME

RELATED APPLICATIONS

This application is a division of application Ser. No. 07/825,035 filed Jan. 24, 1992, now abandoned and a continuation-in-part of all of the following applications: U.S. patent application Ser. No. 07/743,152, filed Aug. 9, 1991, now U.S. Pat. No. 5,366,755, U.S. patent application Ser. No. 07/567,045 filed Aug. 10, 1990, now abandoned, U.S. patent application Ser. No. 07/565,346 filed Aug. 10, 1990, now abandoned, U.S. patent application Ser. No. 07/730,029 filed Jul. 12, 1991, now abandoned, U.S. patent application Ser. No. 07/464,291 filed Jan. 12, 1990, now abandoned, U.S. patent application Ser. No. 07/370,629 filed Jun. 23, 1989, now abandoned, U.S. patent application Ser. No. 07/309,387 filed Feb. 10, 1989, now abandoned. The contents of each of the above-identified applications are hereby expressly incorporated by reference.

The contents of Applicants' related applications entitled "Paper Composition and Uses Therefor" filed concurrently herewith, and U.S. patent application Ser. No. 07/566,013 filed Aug. 10, 1990, now abandoned are also expressly incorporated by reference.

FIELD OF THE INVENTION

This invention relates to capsules comprised of complex colloidal materials and to a method of making them. Examples of such capsules are microcapsules. In particular preferred embodiments, the invention relates to the use of oligomers of polysaccharide derivatives having a rod-like configuration and oligomeric mixtures which are monodisperse, i.e. mixtures of oligomers extending over a relatively narrow range of molecular weights, preferably having a polydisperity index of less than 2.0.

BACKGROUND OF THE INVENTION

Encapsulation technologies have numerous applications in a variety of industries when it is desirable to isolate a particular material until required. Encapsulation makes possible, for example, the ability to mask unpleasant tastes, to protect substances such as unsaturated fats and oils from oxidation, to control the release of encapsulated material, to convert a liquid material into a free flowing powder, to control flow properties, and to separate reactive materials until a particular reaction is desired. The encapsulated material may be released by mechanical, physical or chemical processes such as increasing the pressure or shear, increasing the temperature, dissolving the capsule wall, or letting the internal phase diffuse through the capsule wall.

Simple coacervation is the phenomenon of phasing a soluble polymer, such as gelatin, out of solution in order to encapsulate dispersed oil globules or solid particles within a uniform, continuous coating. This coacervation can be achieved by controlling the pH, temperature or polymer concentration. A typical procedure is to add a solution of salt to a solution of gelating containing the dispersed oil globules, thereby reducing the solubility of the gelatin causing it to coacervate around the surfaces of suspended oil globules and eventually precipitate out of the solution. The microcapsules may then be separated and dried.

Complex coacervation is a controlled reaction between two oppositely charged polymers to form an insoluble polymeric complex that will precipitate from solution. The most common combinations are gelatin and one of one or more ionic polymers, such as gum arabic, pectin, and microbial polysaccharides (e.g. gellan gum). In food products, gelatin-gum arabic coacervates have been used to encapsulate flavors for inclusion in cake mixes, chewing gum, confectionary and other products.

Complex coacervation, however, requires complicated steps and a strict control of process parameters such as pH and temperature. Although gelatin is used for most of the complex coacervation procedures because it has good amphoteric properties as well as the ability to gel at temperatures above refrigeration, the structural network formed may not have sufficient structural integrity when high molecular weight ionic polysaccharides such as gum arabic, carboxymethyl cellulose, and synthetic ionic polymers are used. Conventional high molecular weight polymers or oligomers used in encapsulation procedures have a number of other disadvantages. Such polymers give very high viscosity suspensions even at low concentrations and therefore limit the concentration of polymer that can be used in the encapsulation process. This makes the process difficult to carry out in practice. The capsules prepared using high molecular weight polymers are easily broken because the membrane has insufficient strength. In addition, the processing usually takes a long time, up to about 20 to 24 hours or even longer and requires a strict control of the processing conditions.

It is therefore important to provide a method of encapsulation which provides higher quality capsules and a higher yield of capsules. Such a method should be simple to operate and economical.

SUMMARY OF THE INVENTION

This invention relates to the use of polysaccharide derivatives of low molecular weight in encapsulation processes and the capsules thus produced.

Methods of forming the capsules of the invention involve combining at least two polymeric components, wherein one of the components a low molecular weight mixture of polymers or oligomers derived from degradation of a substituted polysaccharide derivative. As known in the art, oligomers refer to polymers having a lower molecular weight or degree of polymerization ("DP") relative to a long or longer chain polymer from which an oligomer or oligomeric mixture is derived. The other polymeric component may be ionizable and oppositely charged and/or may be gellable. The mixture of oligomers derived from degradation of a selected polysaccharide derivative has an average degree of polymerization in the range of about 3 to about 500, preferably 3–300, more preferably 3–100 and most preferably 3–50 at least in the case of CMC. The polysaccharide derivative can be any one of a wide variety of polysaccharides although cellulose, and starch derivatives are preferred.

As to cellulose and starch based materials, the terms polysaccharide and polysaccharide derivative, as used herein, are intended to refer only to cellulose and starch polymers which are substituted with substituents such as carboxymethyl, hydroxypropyl and other substituents as discussed herein. As to polymers or oligomers other than cellulose or starch based materials, the terms polysaccharide and polysaccharide derivative include polymers of sugar monomers such as glucose, galactose, mannose, fructose, etc. which are either substituted or unsubstituted.

As described in detail below, most preferably, the polysaccharide derivative oligomeric mixtures are comprised of a majority of oligomers having a rod-like configuration as opposed to a random-coil configuration, See. FIG. 6. Furthermore most preferably, the oligomeric mixtures have a polydispersity index of less than about 2.0 and contain less than about 25% by weight, most preferably less than about 10% by weight, of monosaccharides, disaccharides and mixtures thereof. As described in examples below, capsules made from high molecular weight or long chain starting materials from which the most preferred oligomeric mixtures are derived do not form suitable capsules according to the invention.

The method of encapsulating materials of the invention comprises combining a polymer and a mixture of low molecular weight polymers derived from degradation of a polysaccharide derivative under conditions sufficient for the polymers to form an insoluble polymeric capsule. The substance to be encapsulated is incorporated into the solution as well and capsules form around the substance. The substance can be introduced in any form capable of being encapsulated, e.g. solid, liquid or slurry. Residual polymer can then be removed. The method of the invention further comprises strengthening the membrane capsule by cross-linking a polymeric component of the capsule with a cross-linking agent, such as glutaraldehyde.

The method includes the steps of forming a mixture of at least two polymers which may be ionic in water. One of the polymers is the low molecular weight polysaccharide derivative oligomer(s) derived from degradation of a long chain polysaccharide derivative and the other polymer may be a polymer capable of forming a membrane with the low molecular weight polymer. The polymers may form a membrane by one or more types of secondary bonds. In the case where the capsule is formed by ionic interactions, an ionizable hydrophillic colloid is employed.

The method also comprises the steps of adjusting the pH so that the polymers are similarly charged; introducing the selected substance to be encapsulated and forming an emulsion by beating or stirring; adjusting the pH of the mixture, if necessary, so that the ions of the two polymers have different electric charges and form droplets or capsules; cooling the emulsion to a temperature below the gelation point of the complex; washing the capsules to remove residual ionic polymer; if desired, hardening and strengthening the encapsulated material by cross-linking the capsules with a cross-linking agent; separating the capsules from the remaining liquid, and, finally, drying them and comminuting them if aggregated. The adjustment or change in pH and lowering of temperature may not be necessary if the encapsulation is accomplished by a simple secondary interaction such as hydrogen bonding or Van Der Waal forces.

The capsules of the invention are designed to contain any compatible substance. Such substances include pharmaceuticals, oils, synthetic oils, mineral oils, vegetable oils and animal oils. The encapsulated material can also be a fluid of an intrinsic color or ink that changes to a color when applied to sensitized record material.

In accordance with the invention, there is provided a capsule created by two polymers, one of which is the low molecular weight polysaccharide derivative of DP 3-500. In a specific case when ionic interactions are the means for encapsulation, an ionic gellable polymer is combined with an oppositely charged, water soluble or water suspendable mixture of oligomers derived from a degraded polysaccharide derivative, the mixture of oligomers having an average degree of polymerization in the range of about 3 to about 500, with an oppositely charged polymer, such as gelatin. The most preferred polysaccharide derivative comprises starch derivative or cellulose derivative. The polysaccharide derivative may be degraded by enzymatic, chemical or physical or mechanical agents/mechanisms. In embodiments where an enzyme preparation is utilized to perform the degradation, the enzyme preparation is typically selected from the group of polysaccharide degrading enzymes. In the case of starch derivatives, enzymes such as amylases or pullulanases and mixtures thereof are suitable.

In embodiments where degradation of a polysaccharide derivative is to be effected by chemical or physical means, chemical hydrolysis, chemical oxidation and heat treatment are preferred mechanisms for achieving the desired polymeric mixtures according to the invention.

This invention further provides a pressure-sensitive paper to which is affixed oil, or ink containing capsules of the invention.

DETAILED DESCRIPTION OF THE INVENTION

Figure 1:
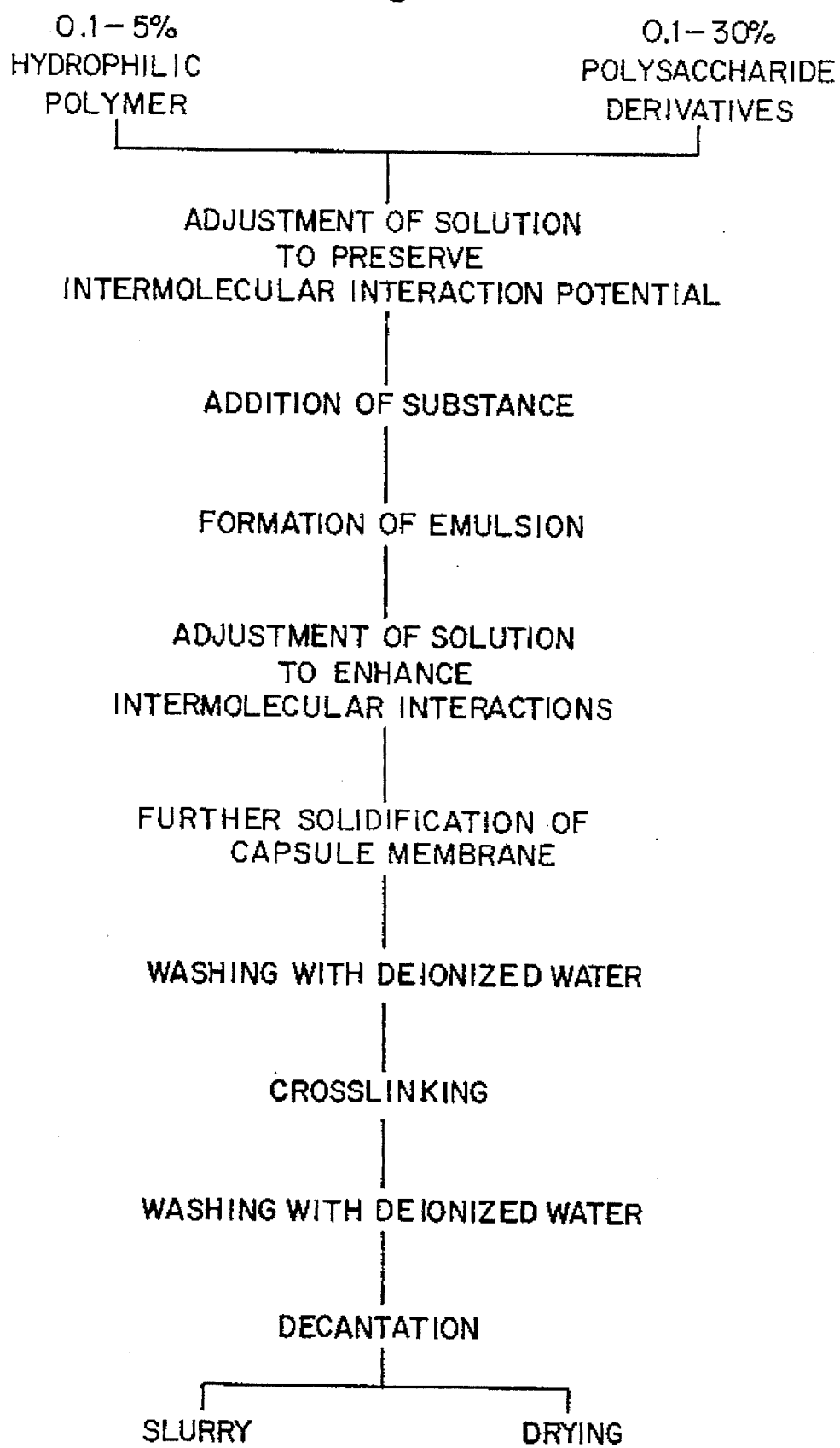
FIG. 1 schematically illustrates a method of forming capsules having a substance incorporated within the capsules.

In broad outline, the method of the invention comprises combining at least two polymers under conditions sufficient to form capsules. One of the components may be an ionizable, hydrophilic material such as gelatin. The other component may be a charged polymer derived from at least one substituted polysaccharide derivative, which polymer is derived from the degradation of the polysaccharide derivative and has an average degree of polymerization in the range of about 3 to about 500, preferably 3–300, more preferably 3–100, and most preferably 5–50 as described more fully below.

The C-O-C linkage formed between two joined simple sugar units in a polysaccharide chain is called a glycosidic linkage, and continued condensation of monosaccharide units will result in polysaccharides. The most common polysaccharides are amylose and cellulose, both made up of glucose monomers. Amylose is a major constituent of starch and glycogen. Cellulose is the major structural component of plants. Other polysaccharide derivatives useful in this invention have a straight chain or branched polymer backbone including one or more sugar monomers. These polysaccharides include those having sugar monomers such as glucose, galactose, arabinose, mannose, fructose, rhamnose, and xylose.

Most preferred polysaccharide derivatives useful in the article and methods of this invention are cellulose derivatives and starch derivatives. Examples of other such polysaccharide derivatives with branched or straight backbones are carrageenan, pullulan, pustulan, laminarin, scleroglucan, alginate, guar gum, gum arabic, inulin, pectin, whelan, rhamsan, gellan, xanthan, zooglan, methylan, chitin, cyclodextrin, chitosan, hemicellulose and beta-glucan.

Preferably, a polysaccharide derivative starting material having substituents has a degree of derivatization or substitution of between about 0.1 and about 3.0. "Degree of substitution" refers to the number of derivative or substituent groups (e.g. carboxymethyl, hydroxypropyl) per monomer unit in the polysaccharide backbone (branched or straight chain backbone). A degree of substitution of 0.2 means for example that there is about one derivative substituent for every five monomer units in the polysaccharide backbone. A degree of substitution of three would mean there are three derivative substituents per every monomer unit in a polysaccharide chain. The term "substituent" is meant to include any group attached to the polysaccharide backbone that imparts some chemical and/or physical property to the polysaccharide or provides some functional effect.

Typical substituents comprise one or more of sulfate, carboxylic acid (as found, for example, in carragenan, alginate, pectin), carboxylic ester, pyruvic acid (as found, for example, in pectin, xanthan gum, zooglan, and methylan), carboxymethyl, hydroxypropyl, methyl, methylethyl, hydroxyethyl, hydroxyethylmethyl, hydroxypropylmethyl and the like.

Carboxymethyl starch can be degraded enzymatically to produce corresponding starch hydrolyzates. Other typical suitable starch derivatives include hydroxypropyl, methylethyl and hydroxyethyl starches. The substituents are typically bonded to a starch glucose monomer unit at the 2, 3 and 6 positions. Most typically a starch starting material comprises between about 1% to 85% amylose and about 15% to 99% amylopectin.

Cellulose derivatives are commercially available. Examples of cellulose derivatives include methylcellulose (MC, Methocel MC, 64630, Fluka Chemie AG, CH-9470 Buchs, Switzerland), hydroxypropylmethylcellulose (HPMC, H-9262, Sigma Chem. Co., St. Louis, Mo.) and carboxymethyl cellulose (CMC 7MFD, Blanose, Hercules Chem. Co., 92507 Rueil-Malmaison Ceder, France) all have a degree of substitution between 0.1 and 3. Hydroxypropyl celluloses are also commercially available and suitable for use.

As described more fully herein, such polysaccharide derivatives may be degraded to polymeric mixtures of average DP between about 3 and about 500 by enzymatic, chemical or physical or mechanical agents/means. The polymeric mixtures are generally referred to as a "hydrotyzate." The term "degraded" refers to the procedure whereby polysaccharide derivatives are broken down into a mixture of smaller oligomeric units.

Exemplary enzymes for use in degrading certain of the above described polysaccharide derivatives are pectinases, lyases, xanthanases, lysozymes, chitinases and laminarinases. Exemplary enzymes which are suitable for degrading cellulose derivatives are various cellulases. They can be produced from a multitude of different microorganisms such as strains of Trichoderma, Aspergillus, Penicillium, etc. A selected microorganism strain is grown by conventional means in medium containing food grade materials such that the cellulases are produced, the microorganism is separated from the medium, the medium is collected and typically concentrated and dried. These enzymes can be used as such or in mixtures and they can be modified in many different ways known to those skilled in the art.

A polysaccharide derivative may be hydrolyzed by treatment with a solution of acid. Typical acid treatment solutions might contain acids such as sulphuric acid, hydrochloric acid, phosphoric acid, or mixtures of the foregoing. The concentration of the acid in the treatment solution and the treatment time and temperature may vary depending on the degree of degradation of the polysaccharide derivative which is desired. In any event where an acid hydrolysis treatment is utilized, the acid concentration and the treatment time and temperature is selected to produce a mixture of polymers having an average DP of between about 3 and about 500.

A selected polysaccharide (e.g. starch or cellulose) derivative may be degraded by oxidation with such agents as chlorine, oxygen or hydrogen peroxide. Such oxidative treatments and reaction conditions are well known in the art. It may also be possible to use physical methods like heat or mechanical shear treatment or sonication when cleaving the chain backbone of polysaccharide derivatives.

Whatever conventional chemical (hydrolytic, oxidative or otherwise) or physical treatments are employed, the conditions and the degree of treatment are selected such that the polymeric mixture resulting from the initial treatment has an average DP of between about 3 and about 500, preferably 3 to 300, more preferably 3–100 and most preferably 5–50 at least with respect to CMC as described below.

Enzymes which may be used with respect to capsules prepared with degraded starch derivatives, are various amylolytic enzyme preparations. They can be produced from a multitude of different microorganisms such as strains of Bacillus, Klebsiella, Clostridium, Aspergillus, Rhizopus. Typical commercially available enzyme preparations suitable for use herein are amylolytic preparations (such as alpha and beta amylases), pullulanases, and cyclodextrin glycosyltransferase (CGTase).

The polymers described above are used in the method of the invention to form capsules. The term "capsule" is broadly meant to define roughly spherical and hollow objects having walls formed of polymeric material capable of surrounding substances such as liquids, solids, or slurries.

The substance may act as a seed or nuclei to stimulate formation of the capsules. The capsules formed by the process of the invention can vary widely in size. The capsule may range from less than about 10µ to about 500µ in diameter with a probable wall thickness of about 2µ to about 10µ. Capsules can be as large as millimeter size.

The most preferred method comprises mixing together at least two polymeric components. One of these components is the substituted polysaccharide polymers described above having an average degree of polymerization in the range of about 5–500. At least one other of these components may be an ionizable hydrophilic material having an opposite electric charge to the substituted polysaccharide polymers. The term "ionizable hydrophilic material" is meant to include ionizable materials. This material can be gellable. Examples of the ionizable hydrophilic materials used to form the capsules of the invention can include gellable substances such as gelatin, albumin, casein, alginates, agar, pectins, gum arabic and gellable proteins generally.

In general, the capsules are caused to have deposited within them substances designed to be encapsulated. These encapsulated substances are centrally located in the capsule. The term "substance" can include any material or any that is capable of producing a desired effect in the particular environment or of performing a desired function. Capsules of the invention can preferably contain oil or oil-phase substances. The term "oil" or "oil-phase substances" is meant to include any water immiscible fluid such as natural occurring oils (olive oil, coconut oil, castor oil, fish oil, animal oils, vegetable and mineral oils) as well as synthetic oils such as methyl salicylate, and the like.

Capsules of the invention can also include bioactive substances.

The expression "bioactive substances" as used herein broadly includes any compound, or mixture thereof, that can be delivered from the capsule to produce a beneficial result. The bioactive substances can be soluble or it can have limited solubility in the capsule, such as an oil phase, powder, or other solid form. The term "bioactive substance" includes pesticides, herbicides, germicides, biocides, algicides, rodenticides, fungicides, insecticides, antioxidants, plant growth promoters, plant growth inhibitors, preservatives, disinfectants, sterilization agents, catalysts, chemical reactants, fermentation agents, foods, animal feeds, food or animal feed supplements, nutrients, cosmetics, drugs, vitamins, sex sterilants, fertility inhibitors, fertility promotors, air purifiers, microorganism attenuators, and other agents that benefit the environment of use.

The term "drug" includes any physiologically or pharmacologically active substances such as pharmaceuticals that produce a localized or systemic effect or effects in humans and other animals.

The term "animal" includes, but is not limited to, mammals and primates. Examples include domestic household, sport or farm animals such as sheep, goats, cattle, horses, pigs, for administering to laboratory animals such as mice, rats and guinea pigs, and to fishes, to avians, to reptiles and zoo animals.

The term "physiologically" as used herein denotes the administration of drug to produce normal levels of functions. The term "pharmacologically" denotes the study of the actions of pharmaceutical on living systems, including therapeutics, as defined in Dorland's *Illustrated Medical Dictionary,* 1974. Published by W. B. Sanders Co., Philadelphia, Pa.

The bioactive substances that can be incorporated into the capsules of the invention include inorganic and organic compounds without limitation, including drugs that act on the peripheral nerves, adrenergic receptors, cholinergic receptors, nervous system, skeletal muscles, cardiovascular, smooth muscles, blood circulatory system, synaptic sites, neuroeffector junctional sites, endocrine and hormone systems, immunological system, reproductive system, skeletal system, alimentary and excretory systems, inhibitory and histamine systems, and those materials that act on the central nervous system such as hypnotics and sedatives.

Examples of beneficial pharmaceuticals are disclosed in Remington's *Pharmaceutical Sciences,* 16th Ed., 1980, published by Mack Publishing Co., Eaton, Pa.; and in the *Pharmacological Basis of Therapeutics,* by Goodman and Gilma, 6th Ed., 1980, published by the MacMillan Company, London; and in *The Merck Index,* 10th Ed., 1983, published by Merck & Co., Rahway, N.J.

The dissolved pharmaceutical can be an ionizable salt. Acceptable salts include, but are not limited to, hydrochlorides, hydrobromide, sulfate, laurylate, palmitate, phosphate, nitrate, borate, acetata, maleate, tartrate, oleate, salicylate, salts of metals, and amines or organic cations, for example quarternary ammonium.

The process of the invention is shown in FIG. 1. The method includes the steps of forming a mixture of at least two ionic polymers in water; at least one of the polymers may be an ionizable hydrophilic colloid and at least one other polymer is a mixture of charged polysaccharide derivative oligomers, as described herein; adjusting the pH to above the isoelectric point; introducing the selected substance to be encapsulated and forming an emulsion by beating or stirring; adjusting the pH of the mixture, if necessary, so that the ions of the two polymers have different electric charges and form coacervate droplets or capsules; cooling the emulsion to a temperature below the gelation point of the complex; washing the capsules to remove residual ionic polymer; if desired, hardening and strengthening the encapsulated material by cross-linking the capsules with a cross-linking agent; separating the capsules from the remaining liquid, and, finally, drying them and comminuting them, if aggregated.

In preferred embodiments, the charged polysaccharide derivative oligomers described above are complexed with a gellable ionic polymer such as gum arabic or gelatin. Gelatin is particularly preferred for this procedure. Preferably, aqueous solutions of gelatin and charged polysaccharide polymer derivative hydrolyzates are mixed in the volume ratio of 1:1 at a pH above the isoelectric point. The pH can be adjusted with any compatible base, for example, sodium hydroxide or ammonium hydroxide, at a temperature above the gelation point of gelatin. Preferably, this temperature is between about 30° C. and about 70° C. depending on the molecular weight of the gelatin.

Concentrations of gelatin and charged polysaccharide derivative hydrolyzate solutions may typically vary from 0.1 to 5 percent (w/v) of gelatin and from about 0.1 to about 30 percent (w/v) solution of charged polysaccharide derivative hydrolyzate, depending on the average degree of polymerization of the oligomeric mixture.

Substances to be encapsulated is then added to the gelatin-polysaccharide solution in a volume ratio between about 1:2 to about 1:0.8. The solution is continually stirred or beaten during the incorporation of the substance to form a dispersion. When a dispersion is formed, the pH is reduced to about 3 or 4.5. Preferably, the pH is reduced to 4.0 using an acid such as hydrochloric acid. At this pH, gelatin acquires an overall positive charge which enables electrostatic interaction to occur between the gelatin and the polysaccharide derivative.

After adjusting the pH, the dispersion is cooled to about 10° C.–30° C. Preferably, about 10° to about 15° C. may be used.

The resulting capsules will gel at temperatures below the gelation point of the complex. Capsules formed by this procedure can then be washed with water to remove any residual gelatin. After this, the membrane of the capsule can be strengthened using various procedures.

Preferably, the gelatin component of the membrane is strengthened by cross-linking it with various cross-linking agents. Preferred cross-linking agents are dialdehyde, formaldehyde, glutaraldehyde and ascorbic acid. Solutions of cross-linking agents such as glutaraldehyde at 0.25 percent to 6 percent (w/v) final concentration are then added to the dispersion and the entire dispersion is vigorously stirred from 10 to about 20 minutes. The stirring, in combination with cross-linking agents promotes hardening of the capsules. Capsules can then be washed with water and dried.

An extremely wide variety of substances can be added to the mixture of charged polysaccharide derivative and gelatin. For example, food products such as fats, vitamins, minerals, and the like can be used. Synthetic oils, mineral oils, vegetable oils, and animal oils may be used such as, for example, methylsalicylate, petroleum oil, coconut oil, castor oil and sperm oil.

Other materials can be encapsulated by the method of this invention. Oils can be encapsulated that can be transferred to an underlying sheet by printing or marking pressure or heat that ruptures the capsules of the invention. "Printing or marking pressures" are meant to define art-recognized procedures for applying pressure. Examples include the use of pens, typewriters, computer-driven graphics, printers and the like. The capsules are fixed to transfer film and pressure on the transfer film will cause marks on the underlying sheet. Examples of such oily printing fluids are chlorinated diphenyls as well as the oils mentioned above. Other dye materials can be incorporated into the oils used in transfer films such as Sudan III or Sudan IV.

Capsules produced by the method of the invention can be completely or partially coated on paper by commonly used procedures such as rolling, brushing or spraying. The capsules will adhere to the paper after drying.

In one embodiment, a sheet of paper is coated with the capsules of the invention. The capsules have within them an oily printing fluid combined with a colorless reactant that turns to a colored form on contact with a record material sensitized with a clay-like substance such as attapulgite or zeolite material. Methods of forming these pressure-sensitive papers are well-known in the art. See Green, U.S. Pat. No. 2,712,507, incorporated herein by reference.

Capsules of this invention can also be provided with oils for food preparation purposes. Capsules can be formed with, for example, cooking oil such as vegetable oil. Food to be cooked can be completely or partially coated with a myriad of these capsules. The heat of a broiling or baking oven can release the cooking oil directly from the interior of the capsule to the food that is to be cooked.

Furthermore, complete capsules or capsules ruptured by heat, pressure and the like may fuse together and completely or partially coat a material to form a continuous membrane on the surface of the material coated with the capsules. This membrane can improve mechanical, textural or functional properties of the product such as strength, taste, water retention and the like.

Capsules produced by the method of the invention can also be used to confine medicinal oils or bioactive substances, as defined above, to prevent them from being tasted upon being swallowed by a patient, to protect them from the deleterious influence of environmental conditions or from contamination.

The invention will now be more fully described by the following examples.

Example 1: General Preparation of a Cellulose Precursor Hydrolyzate

Cellulose derivative hydrolyzates may be prepared from soluble cellulose derivatives as discussed above by an enzymatic hydrolysis utilizing a cellulase preparation having endo-1, 4-beta-glucanase as the sole active hydrolytic agent such that only insignificant amounts of mono- and disaccharides which are absorbed in human intestine (e.g. glucose) or hydrolyzed by the intestinal bacterial flora (e.g. cellobiose), are produced. On the other hand the average degree of polymerization (DP) of the polymers formed by such a hydrolysis is less than about 500, and thus the viscosity of solutions of the hydrolyzate is reduced significantly compared to the viscosity of solutions of the unhydrolysed cellulose derivatives. The specific conditions suitable for and the specific time sufficient to secure the desired hydrolysis may be readily determined for each selected cellulose derivative and each selected enzyme preparation.

Similarly in other embodiments of the invention where degradation is carried out using chemical or physical means, the average DP of the polymers is less than 500 and the viscosity of the resulting mixture is significantly reduced.

The absolute amount of enzyme used in any particular example is hereafter reported in terms of the universal activity unit of nano-katal (nkat). "nkat" refers to that amount of enzyme which produces one nanomole of reaction product in one second. Specifically the context of this application, nkat units refer to a hydrolyzate reaction product such as a polymer which is capable of reducing an agent such as dinitrosalicylic acid. The method of Bailey et al., *Enzyme Microb. Technol.*, Vol. 9, pp. 153–157 describes how such measurements of enzyme activity can be made using glucose as a standard.

Example 2: Preparation of Typical Cellulose Derivative Enzyme Hydrolyzates Containing Small Amounts of Mono- and Disaccharides and Having Low Viscosity a. Methylcellulose hydrolyzate 30 g of methylcellulose (MC, Methocel MC, 64630, Fluka Chemie AG, CH-9470 Buchs, Switzerland) was mixed in 3 l of water and the pH of the solution was adjusted to 5.5 with 15% phosphoric acid and the temperature was raised to 40° C. 0.3 ml of an enzyme preparation from *Trichoderma reesei*, Econase CE (as so designated by Alko Ltd., Helsinki, Finland) having a total endo-1, 4 beta-glucanase activity of 1680 nkat from which the beta-glucosidase activity was removed chromatographically was added to the solution. After hydrolysis for 24 hours the enzyme was inactivated by heating (90° C., 15 min.). The hydrolyzate solution was subsequently cooled and freeze-dried.

The hydrolyzate product contained less than 0.5% by weight of glucose and cellobiose.

b. Hydroxypropylmethylcellulose hydrolyzate 20 g of hydroxypropylmethylcellulose (HPMC, H-9262, Sigma Chemical Company, St. Louis, Mo., U.S.A.) was mixed in 1 l of water and the pH of the solution was adjusted to 5.5 with 15% phosphoric acid and the temperature was raised to 40° C. 0.24 ml of the enzyme preparation (Econase) described above having a total endo-1, 4 beta-glucanase activity of 1340 nkat from which the beta-glucosidase activity was removed chromatographically was added to the solution. After two hours another 20 g of hydroxypropylmethylcellulose was added to the solution. After the hydrolysis of 22 hours the enzyme was inactivated by heating (90° C., 15 min.). Finally the hydrolyzate solution was cooled and freeze-dried.

The product contained less than 0.05% by weight of glucose and cellobiose.

c. Carboxymethyl cellulose hydrolyzate
  (i) Hydrolysis with *Trichoderma reesei* derived enzyme preparation 20 kg of carboxymethyl cellulose (CMC 7MFD-type, a cellulose gum, also designated by the tradename Blanose and available from Hercules Chemical Company, 92507, Rueil-Malmaison Ceder, France; 7MFD designating a medium viscosity, food grade carboxymethyl cellulose having 7 out of 10 glucose units substituted with carboxymethyl) was mixed in 320 l of water and the pH of the solution was adjusted to 5.5 with 15% phosphoric acid and the temperature was raised to 40° C. 0.27 l of the enzyme preparation (Econase) described above having a total endo-1, 4 beta-glucanase activity of 1,780,000 nkat from which the beta-glucosidase activity was removed chromatographically was added to the CMC solution. After one hour another 23 kg of CMC was added to the solution. After hydrolysis of 23 hours the enzyme was inactivated by heating (90° C., 15 min.). Finally, the hydrolysis solution was concentrated by conventional evaporating and spray-drying.

The product contained less than 2% by weight of glucose and cellobiose. When the same hydrolysis was carried out with the original cellulase enzyme preparation of *Trichoderma reesei*-fungus, the amount of produced glucose and cellobiose was above 5% by weight.

(ii) Hydrolysis with Aspergillus and Penicillium derived enzyme preparations

The enzyme preparations selected were commercially available Cellulase AP 3 (Amano Pharmaceutical Co., Ltd., Nagoya, Japan) produced using an Aspergillus strain and Cellulase CP (Sturge Enzymes, North Yorkshire, England) produced using a Penicillium strain. Carboxymethyl cellulose hydrolyzates were prepared as described in Example c(i), except that 30 g of CMC-7MFD was used in 1 l of water, and the amounts of enzymes added were 0.028 g of Cellulase AP 3 (having a total endo-1, 4 beta-glucanase activity of 1350 nkat) and 0.048 g of Cellulase CP (having a total endo-1, 4 beta-glucanase activity of 1350 nkat). The viscosities and molecular weight distributions of the hydrolyzates produced by either cellulase were similar to the hydrolyzate produced with enzymes derived from *Trichoderma reesei*.

The viscosities of the various cellulose derivatives and their hydrolyzates as described above were measured using a Haake-Rotovisco viscometer with sensor systems NV (Karlsruhe, Federal Republic of Germany) (Table 1). The viscosities were measured in water solutions at 25° C. Table 1 sets forth the concentrations (by weight) of a variety of solutions all having the same viscosity.

TABLE 1

Concentrations of cellulose derivatives and their respective hydrolysates in solution all having a viscosity of 20 mPa · s (milli-Pascals-second) at 25° C.

| Cellulose Derivative | Concentration (by weight) |
|---|---|
| Methylcellulose | 2% |
| Methylcellulose hydrolysate | 5% |
| Hydroxypropylmethylcellulose | 3% |
| Hydroxypropylmethylcellulose hydrolysate | 10% |
| Carboxymethylcellulose | 2% |
| Carboxymethylcellulose hydrolysate | 20% |

As the data in Table 1 indicates, the hydrolyzate of a cellulose derivative has a substantially lower viscosity than an equal amount by weight in aqueous solution of the cellulose derivative starting material itself. As described below, in most preferred embodiments oligomeric mixtures have a viscosity low enough such that the oligomers have a rod-like configuration.

Example 3: Carbomethylcellulose Chemical Hydrolysis 2 gms of carboxymethyl cellulose (Blanose Cellulose Gum 7 LFD, Hercules Chemical Co., 92507, Rueil-Malmaison Cedar, France) was hydrolyzed for about one hour in 100 ml of 1M sulphuric acid solution at about 100° C. After hydrolysis the solution was cooled to about room temperature, neutralized to about pH 6 with 25 ml of 25% (w/w) of NaOH solution and freeze-dried. This hydrolysis treatment produced a mixture of oligomers containing less than about 4% by weight of mono- and disaccharides (cellobiose and glucose). The viscosity (and average DP) of this hydrolyzate is similar to the viscosities (and average DP) of the hydrolyzates produced by the enzymatic treatments described above utilizing enzymes derived from *Trichoderma reesei*.

Rod-Like Configuration of Preferred Oligomers

Chain conformation of oligomers can be evaluated from the molecular weight (or DP) dependency of intrinsic viscosity of a solution of oligomers using the Mark-Houwink equation:

$$[\mu] = KM^a$$

where $[\mu]$ is the intrinsic viscosity, M is the molecular weight, and K and a are constants. The constant a of this equation provides an indication of the chain conformation of a polymer or oligomer. The DP of an oligomer or average DP of a mixture of oligomers is simply calculated from the molecular weight of the oligomer(s) divided by the molecular weight of a monomer unit of the oligomer (about 220 for CMC).

Initially, approximate viscosity average molecular weights ($M_v$) and average DPs of a series of typical CMC oligomeric mixtures designated EP 1511, 1512, 151/49, 151/51, 151/52 were first calculated from the Mark-Houwink equation basedon previously reported literature values (Brown and Henley, 1964) for the K and a components of the equation. Such calculated molecular weights and average DPs are reported in Table 2.

Subsequently the weight average molecular weights ($M_w$) of a variety of typical oligomeric mixtures according to the invention (including one or more of the EP 151 series of preparations described below) were experimentally determined and the K and a values of the Mark-Houwink equation were determined by plotting (e.g. FIG. 7) as described below. The experimentally determined data demonstrate that the unique advantages of preferred oligomeric mixtures according to the invention have not previously been utilized or known. For purposes of illustration, the method of preparation of EP 1511, 1512, 151/49, 151/51, 151/52 according to the invention is described in detail immediately below.

a. CMC Hydrolysate EP1511 was prepared as described in Example 2c(i) hereinabove.

b. CMC Hydrolysate EP1512

20kg of carboxymethylcellulose (CMC 7LFD-type, a cellulose gum, also designated by the tradename Blanose and available from Hercules Chemical Company, 92507, Rueil-Malmaison Ceder, France, 7LFD designating a low viscosity, food grade sodium carboxymethylcellulose having 7. out of 10 glucose units substituted with carboxymethyl group) was mixed in 250l of water and the pH of the solution was adjusted to 5.8 with 15% phosphoric acid and the temperature raised to 40° C. 0.177l of the above-described Trichoderma (Econase) enzyme preparation, having a total endo-1, 4 beta-glucanase activity of 1,780,000 nkat, was added to the CMC solution. After one hour another 20 kg of CMC was added to the solution. After hydrolysis for 23 hours the enzyme was inactivated by heating (90° C., 15 min.). Finally, the hydrolysis solution was concentrated by spray-drying.

c. CMC Hydrolysate EP151/49

6 kg of sodium carboxymethylcellulose (CMC Finnfix 5, available from Metsä-Serla, Chemical Division, SF-44100 Äänekoski, Finland, representing food grade purity and having a degree of substitution between 0.6–0.8) was mixed with 240l of water. The pH of the solution was adjusted between 5.5 and 5.9 with 15% of phosphoric acid and the temperature was maintained at 40° C. 65ml of the above-described Trichoderma (Econase) enzyme preparation, the endo-β-1,4-glucanase activity of which totalled 539,000 nkat, was added to the CMC solution. After an hour another 6 kg of CMC was added. After hydrolysis for 23 hours, the enzyme was inactivated by heating the solution (90° C., 15 min.). The hydrolysate was then concentrated by spray-drying.

d. CMC Hydrolysate EP151/51

6 kg of sodium carboxymethylcellulose (CMC Finnfix 5) was mixed with 240l of water. Temperature and pH were as described with reference to preparation of EP151–49 (40° C., pH 5.5–5.9). 130ml of the Trichoderma (Econase) enzyme preparation, the endo-β-1,4-glucanase activity of which totalled 1,079,000, was added to the CMC solution. After two hours another 6 kg of CMC was added. After hydrolysis for 47 hours the enzyme was inactivated by heating the solution (90° C., 15 min.). The hydrolysate was then concentrated by evaporating and spray-drying.

e. CMC Hydrolysate EP151/52

This hydrolysate was produced as described with reference to EP151–51, except that 195ml of the enzyme preparation containing an endo-β-1,4-glucanase activity of 1,618,000 nkat was used, and the hydrolysis time was 24 hours.

Chain Conformation Based on Prior Literature

The viscosities, the intrinsic viscosities, the viscosity average molecular weights ($M_v$) and the average degrees of polymerization of these various hydrolysate products are set forth in the following Table 2. As noted above, the average $M_v$ values set forth in Table 2 are calculated values. In general, suitable CMC oligomeric mixtures typically have an intrinsic viscosity of between about 50 ml/g and 3 ml/g in 0.2M sodium chloride and a viscosity value between about 5 and about 100 mPas (in 20% by weight solution at 25° C., shear rate $584_s^{-1}$. The viscosities were determined using a rotational viscometer (Haake Viscotester VT 500 with sensor system NV, Karlsruhe, Federal Republic of Germany). The intrinsic viscosities were measured according to the conventional method (described in Flory, *Principles of Polymer Chemistry*, Cornell Univ. Press, VII-4a, Ithaca, N.Y. (1953), the contents of which are incorporated by reference) at 25° C. by using a calibrated Cannon Fenske capillary viscometer (size 50, Cannon Instrument, State College, Pa., USA). The values of K and a for CMC, which were used in this study, were: K=0.043 in 0.2M NaCl and a=0.74 in 0.2M NaCl as described in the literature reference Brown and Henley, *Studies on Cellulose Derivatives Part IV. The Configuration of the Polyelectrolyte Sodium Chloride Solutions*, Macromol. Chem., Vol. 79, 00. 68–88 (1964) and as plotted in dotted line in FIG. 7.

TABLE 2

| CMC Hydrolysate | Viscosity[1] (mPas) | Intrinsic Viscosity[2] (ml/g) | Average $M_v$ | Average DP |
|---|---|---|---|---|
| 1511 | 32 | 31.4 | 7400 | 39 |
| 1512 | 20 | 22.9 | 4800 | 25 |
| 151/49 | 23 | 18.4 | 3600 | 19 |
| 151/51 | 18 | 14.0 | 2500 | 13 |
| 151/52 | 18 | 14.3 | 2600 | 13 |

[1] 20% (w/w) solution, 25° C., shear rate = 584 s$^{-1}$
[2] measured in 0.2M NaCl, 25° C.

Experimental Determination of Chain Conformation and Polydispersity

It is noted that a variety of methods for determining average molecular weight exist, and therefore the values of average molecular weights determined, as well as the average DP values calculated from them, depend upon the experimental method and the basis of calculation. For example, the number average molecular weight can be determined by end group analysis, osmotic pressure, vapor pressure lowering, boiling point elevation, freezing point depression and size exclusion chromatography. The weight average molecular weight can be determined by light scattering experiment, the viscosity average molecular weight from the size exclusion chromatograph. All these methods can be used for determining the average molecular weight which ultimately leads to the average DP values, although different results will be obtained depending on method and calculation used.

The $M_v$ values reported in Table 2 as determined on the basis of the literature value a=0.74 for CMC at 0.2N NaCl is higher than the true average molecular weights of the CMC hydrolysates listed. Experimental determination of weight average molecular weight ($M_w$) by multi angle light scattering measurement as described below shows that this conventional estimation method based on conventional literature values for k and a is not applicable to low molecular weight or relatively short chain polysaccharide derivative oligomers, i.e. rod-like, which are utilized in the most preferred embodiments of the invention.

Furthermore, the most preferred oligomeric mixtures according to the invention have a relatively narrow range of molecular weights, i.e. are relatively monodispersed, having a polydispersity index ($M_w/M_n$, weight average molecular weight divided by number average molecular weight) of less than about 2.0 and typically less than about 1.8. The weight average molecular weights and number average molecular weights of a variety of CMC hydrolysate samples of different degree of hydrolysis were measured and the polydispersity index of all such hydrolysates was calculated as ranging between about 1.1 and about 1.9. Therefore, the oligomers in a most preferred mixture of oligomers according to the invention extend over a relatively narrow range of $M_w$ and, even as to mixtures having an average molecular weight at or near the upper limit of $M_w$ where the oligomers may begin to assume a random coil configuration, are comprised of a significant portion, preferably a majority, of oligomers having a rod-like configuration.

The following materials were used in the experiments for this study to determine intrinsic viscosity at NaCl concentrations between 0.005 and 0.5N and weight average molecular weights, $M_w$.

I. Sodium Carboxymethyl Cellulose
Raw or Starting Materials:

| Samples | Manufacturer |
| --- | --- |
| Blanose 7HFD | Hercules Chemical Company, France |
| Blanose 7MFD | Hercules Chemical Company, France |
| Blanose 7LFD | Hercules Chemical Company, France |
| Finnfix 5E | Metsa-Serla, Finland |
| Finnfix 2 (Lot No 59135) | Metsa-Serla, Finland |
| Finnfix 2 (Batch 59379-1) | Metsa-Serla, Finland |

Hydrolysates:

| Samples | Descriptions |
| --- | --- |
| 151/70 1 h | hydrolysate of Blanose 7LFD |
| 151/70 2 hrs | hydrolysate of Blanose 7LFD |
| 1511 | hydrolysate of Blanose 7MFD |
| 1512 | hydrolysate of Blanose 7LFD |
| 151/63 1 h | hydrolysate of Blanose 7LFD |
| 151/63 4 hrs | hydrolysate of Blanose 7LFD |
| 151/63 24 hrs | hyrdolysate of Blanose 7LFD |
| 151/47 | hydrolysate of Finnfix 5E |
| 151/51 | hydrolysate of Finnfix 5E |
| 151/46 | hydrolysate of Finnfix 5E |
| 1512 Fr.A | fraction of hydrolysate 1512 |

II. Chemical Reagent
Sodium Chloride (Analytical grade, Mallinckrodt, Paris, Kentucky).

In the experimental determination of $M_w$ values, CMC solutions were prepared in 0.2N NaCl solution at pH of 7. The solutions were passed through an HPLC column, and the light intensity was detected by multiangle laser light scattering using a Wyatt Technology, multiangle laser light scattering instrument, model DAWN-F. The flow rate was 0.2 ml/min. The concentrations of the solutions were detected by refractometer, and the sensitivity of the refractometer was 64. The weight average molecular weights, $M_w$, were determined using appropriate computer software and reported in Table 4.

The chain conformation of the most preferred CMC hydrolysates was studied using the Mark-Houwink equation $[\eta]=KM^a$. Again in the formula the variable $\eta$ is instrinsic viscosity, K is a constant indicating the interaction between polymer and solvent, a is the Mark-Houwink exponent and M is the weight average molecular weight of the polymer.

The Mark-Houwink exponent, a, was determined for each hydrolysate for purposes of classifying the oligomer configurations.

The instrinsic viscosities of the hydrolysates were measured from the concentration dependency of reduced viscosity. The reduced viscosity, specific viscosity divided by concentration of a hydrolysate solution, was determined using a Cannon capillary viscometer. The specific viscosity ($\eta_{sp}$) was calculated using the following formula $$\eta_{sp} = \frac{t}{t_o} - 1$$

wherein t is the flow time of the solution passing through the capillary viscometer and $t_o$ is the flow time of the solvent. The relationship between the reduced viscosity ($\eta_r$) and the concentration (c) is expressed as the following where $[\eta]$ is the intrinsic viscosity:

$$\frac{\eta_{sp}}{c} = [\eta] + k^1 [\eta]c$$

Therefore, the intrinsic viscosity was calculated by plotting the measured reduced viscosity versus various concentrations of hydrolysate solutions and the intercept of the plot at concentration of zero was the intrinsic viscosity of the hydrolysates tested.

Figure 7:
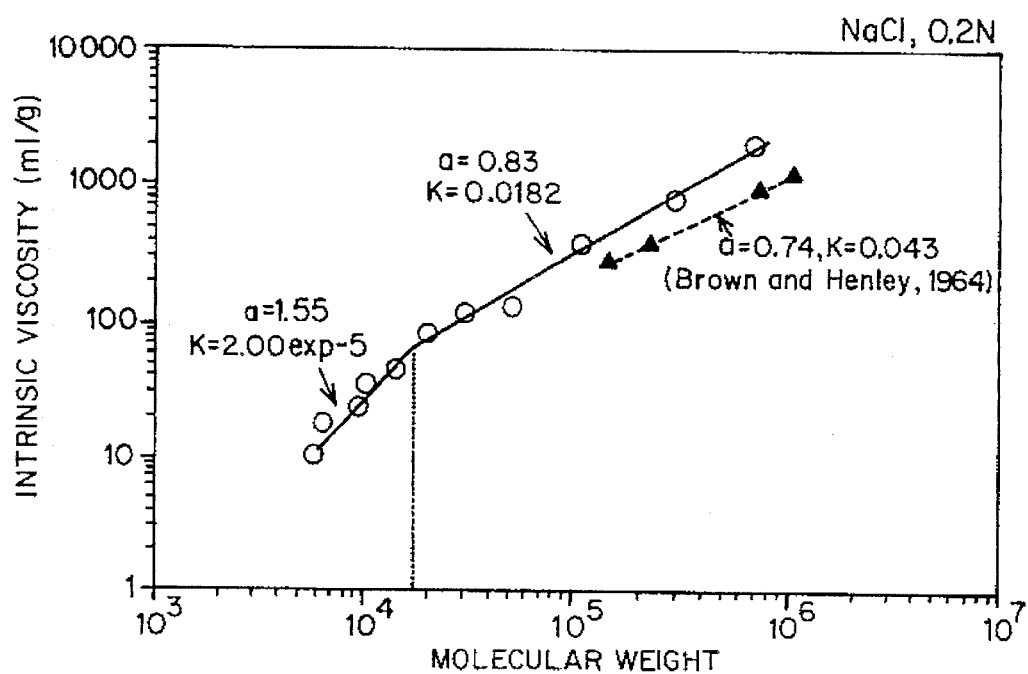
FIG. 7 is a log plot of intrinsic viscosity versus molecular weight as experimentally determined in solid line form for various CMC starting materials (a=0.83, K=0.0182) and hydrolysates (a=1.55, K=2.0 exp −5) in 0.2N solution of NaCl, also showing a dotted line plot for CMC assuming the K and a value for CMC as reported in the literature.

The Mark-Houwink exponent, a, and the constant, K, of the Mark-Houwink equation, $[\eta]=KM^a$, were determined for various CMCs such as listed in Table 4 (in solutions of varying concentration of NaCl) by plotting the log $[\eta]$ versus the log of weight average molecular weight, $M_w$ (e.g. FIG. 7). $M_w$ was experimentally determined by multi angle light scattering instrument measuring as described above. The slope of the plot log $[\eta]$ versus log $[M_w]$ provides the exponent value a and the intercept of the plots at a theoretical log $[M_w]$ of zero provides the value K. The a and K values thus determined are set forth in Table 3.

Chain Conformation

Figure 11:
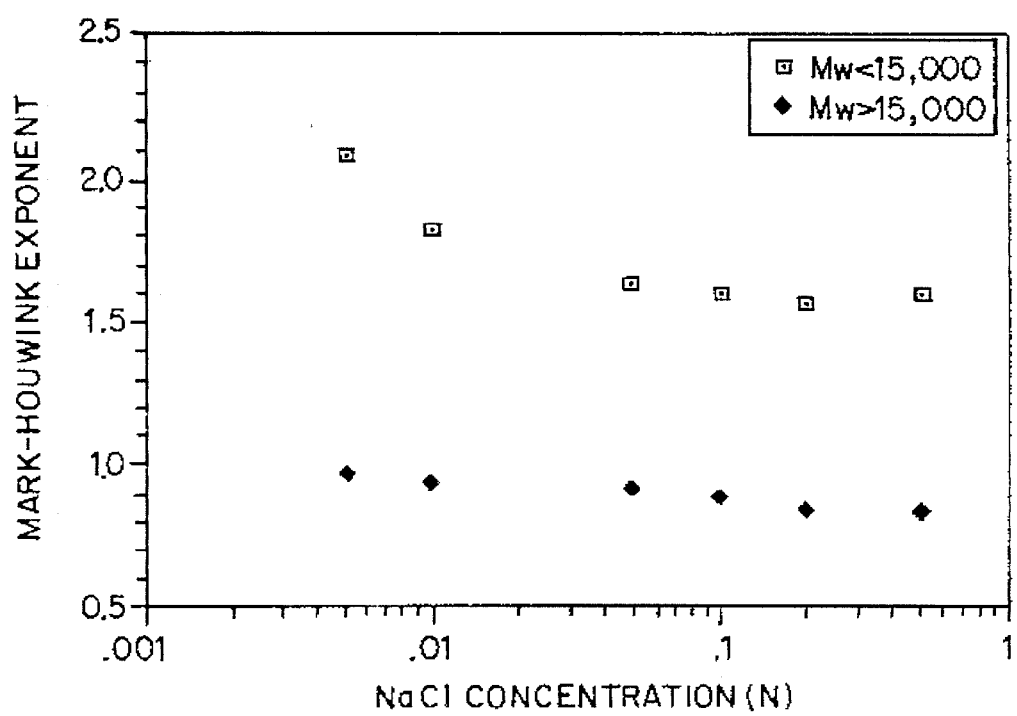
FIG. 11 is a plot of the Mark-Houwink exponent versus the NaCl concentration of CMC raw materials ( ) and CMC hydrolysates (□).

The dependency of Mark-Houwink exponent on differences in salt concentration showed a difference between CMC raw materials and hydrolysates (Table 3 and FIGS. 7 and 11). The Mark-Houwink exponents for CMC raw or starting materials (having $M_w$ greater than about 15,000) are 0.97, 0.94, 0.91, 0.88, 0.83 and 0.83 at NaCl concentrations of 0.005, 0.010, 0.050, 0.100, 0.200 and 0.500N, respectively. In contrast, the Mark-Houwink exponents for CMC hydrolysates (having $M_w$ less than about 15,000) are 2.07, 1.82, 1.63, 1.59, 1.55 and 1.58 at NaCl concentrations of 0.005, 0.010, 0.050, 0.100, 0.200 and 0.500N, respectively. These values are approximately twice (2.13, 1.94, 1.79, 1.81, 1.87, 1.90 times) higher than those of CMC raw materials. The Mark-Houwink exponents of CMC raw materials decreased 14% over the NaCl concentration of 0.005N to 0.50N, while those of hydrolysates decreased 24% over the same range. Therefore, the decrease in the hydrolysates is 1.7 times higher than the CMC raw materials. Mark-Houwink exponents become a constant when the NaCl concentration is higher than 0.2N, probably having reached the unperturbed condition.

Figure 6:
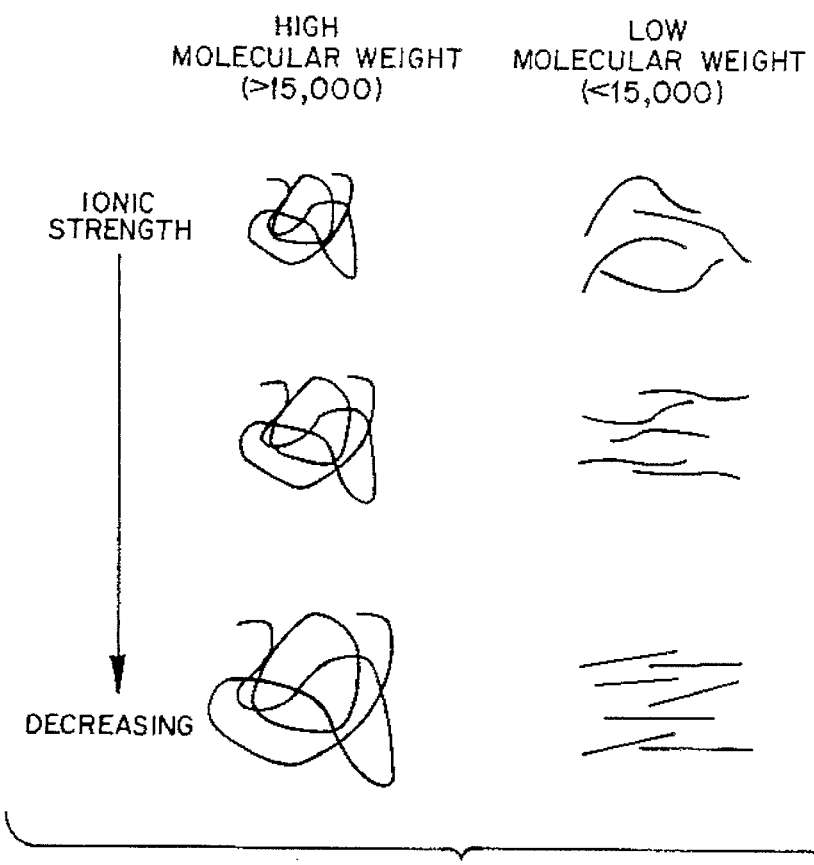
FIG. 6 shows the molecular weight dependent conformation transition in CMC (for both CMC raw materials, $M_w>15,000$, which are used as starting materials to obtain certain hydrolysates described and CMC hydrolysates, $M_w>15,000$)

The Mark-Houwink exponents of 0.83–0.97 for CMC raw material ($M_w$>15,000 Daltons) indicate a free draining random coil conformation (left hand column of FIG. 6). In the random coil conformation, polymer coils are confined by the intra-chain interactions, therefore less change is seen in the Mark-Houwink exponent within the same range of ionic strength. However, when the weight average molecular weight is less than 15,000 Daltons, the CMC chain is not sufficiently long to form a winding coil, the polymer chain is no longer subjected to the constraint of intra-chain interactions, and a chain of free strip or rod-like configuration may form (right hand column of FIG. 6). When the ionic strength is low, the electrostatic repulsion force becomes dominant due to the negative charge of the carboxymethyl groups, and the polymer assumes its most stiff rod-like conformation with the highest value of the Mark-Houwink exponents (Table 3 and FIG. 6). When the ionic strength increases, the negative charge of carboxymethyl groups is shielded, the repulsion forces between the neighboring groups are reduced, and the polymer chains relax, yielding a lower Mark-Houwink exponent (Table 3 and FIG. 6).

The experimentally determined data, as described herein, and with reference to FIGS. 6–11, thus shows that the molecular weight and chain conformational characteristics of the most preferred polysaccharide derivative oligomeric mixtures of the invention, i.e. mixtures comprising a significant or substantial portion of oligomers of rod-like conformation, are distinctly different from polysaccharide polymer compositions previously known or employed in any application. Current understanding of the unique nature and properties of the relatively low molecular weight or short chain oligomers of the most preferred oligomeric mixtures utilized in the invention is lacking. As shown by the experimentally determined molecular weights, $M_w$, of CMC at less than about 15,000 Mark-Houwink a values listed in Table 3 for weight average daltons (a=1.58 to 2.07), the literature value of a=0.74 for CMC is erroneous with respect to CMC having a $M_w$ of less than about 15,000 daltons. This experimentally determined data quantitatively indicates that relatively short chain CMC assumes a rod-like configuration (right hand column of FIG. 6) as opposed to a free draining random coil conformation (left hand column of FIG. 6).

TABLE 3

Mark-Houwink Equations for CMC (25° C.)

| NaCl Concentration (N) | Weight Average Molecular Weight | |
|---|---|---|
| | >15,000 | <15,000 |
| 0.005 | $[\eta] = 0.0069 M_w^{0.97}$ | $[\eta] = 0.02 \times 10^{-5} M_w^{2.07}$ |
| 0.010 | $[\eta] = 0.0084 M_w^{0.94}$ | $[\eta] = 0.17 \times 10^{-5} M_2^{1.82}$ |
| 0.050 | $[\eta] = 0.009 M_w^{0.91}$ | $[\eta] = 0.83 \times 10^{-5} M_2^{1.63}$ |
| 0.100 | $[\eta] = 0.0116 M_2^{0.88}$ | $[\eta] = 1.18 \times 10^{-5} M_w^{1.59}$ |
| 0.200 | $[\eta] = 0.0182 M_w^{0.83}$ | $[\eta] = 2.00 \times 10^{-5} M_w^{1.55}$ |
| 0.500 | $[\eta] = 0.0179 M_w^{0.83}$ | $[\eta] = 1.21 \times 10^{-5} M_w^{1.58}$ |

Chain Stiffness Parameter

Figure 8:
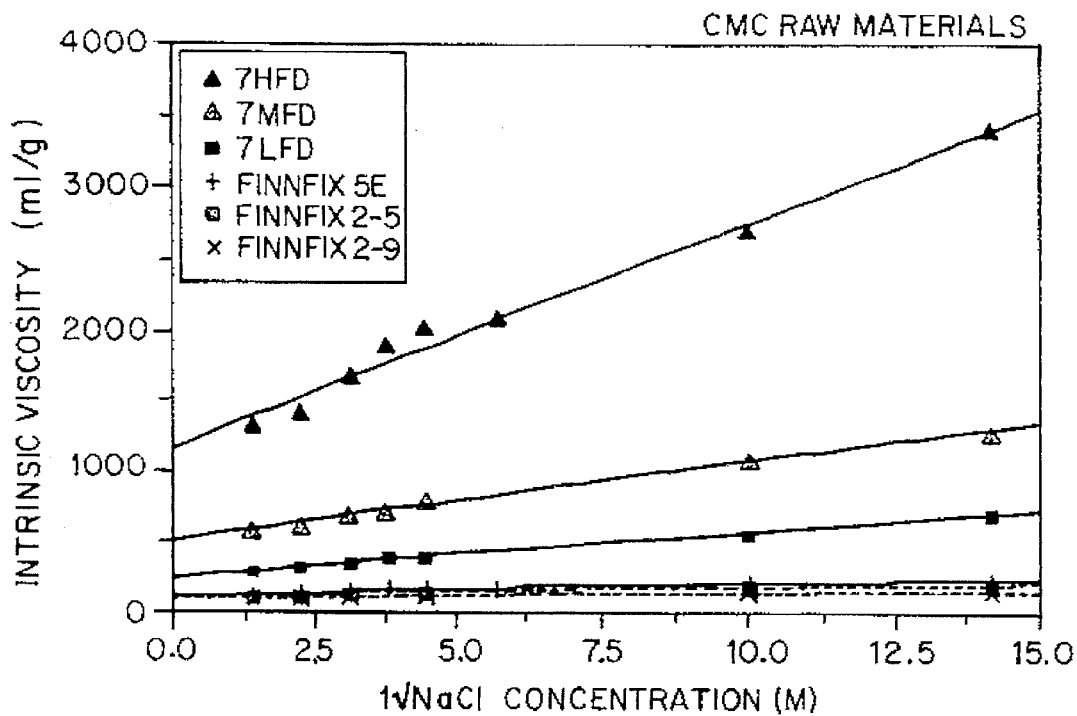
FIG. 8 is a plot of the intrinsic viscosity versus the square root of NaCl concentration of the CMC raw materials.
Figure 9:
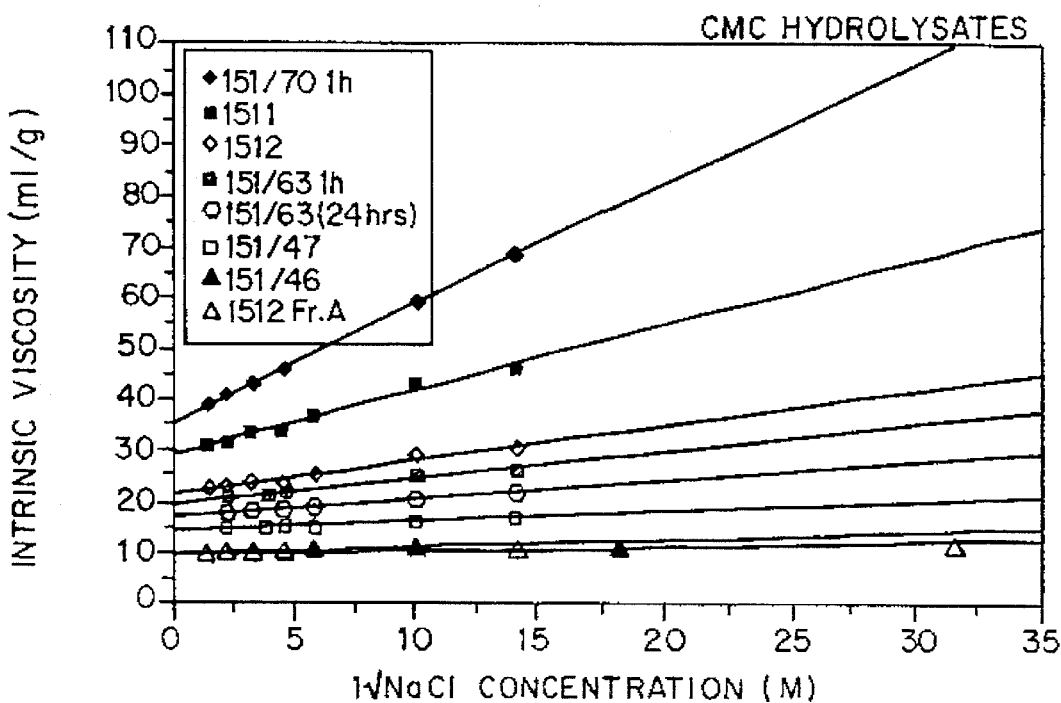
FIG. 9 is a plot of the intrinsic viscosity of the CMC hydrolysates versus the square root of the NaCl concentration.
Figure 10:
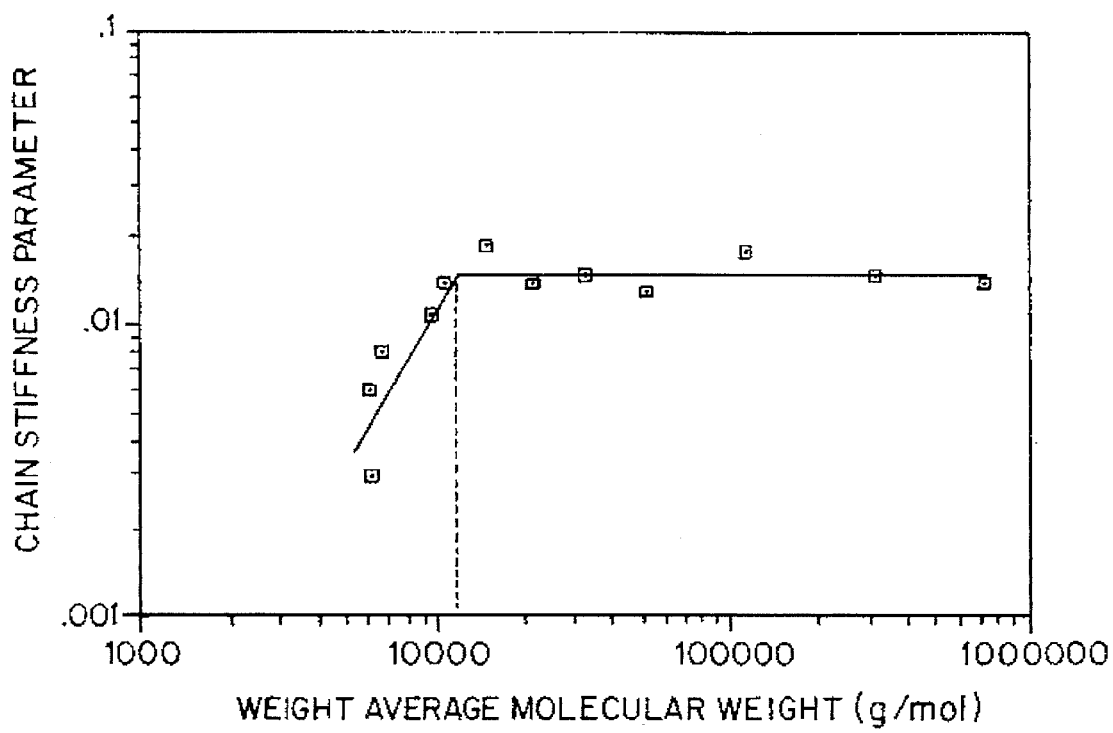
FIG. 10 is a log plot of the chain stiffness parameter versus the weight average molecular weight of CMC showing a transition occurring at a lower molecular weight.

The chain stiffness parameters are 0.014, 0.015, 0.018, 0.013, 0.015, 0.014, 0.019, 0.014, 0.011, 0.010, 0.008, 0.005, 0.006 and 0.003 for Blanose 7HFD, Blanose 7MFD, Blanose 7LFD, Finnfix 5E, Finnfix 2 (Lot# 59135), Finnfix 2 (Batch 59379-1), 70 1h, 1511, 1512, 151/63 1h, 151/63 24hrs, 151/47, 151/46 and 1512 Fr.A, respectively (Table 4). These chain stiffness parameters were calculated from the slopes of the plot between the intrinsic viscosity and the square root of NaCl concentration (FIG. 8 and FIG. 9). The relationship between the chain stiffness parameter and the weight average molecular weight shows a sudden decrease in the chain stiffness parameter when the weight average molecular weight becomes less than 10,000 Daltons (FIG. 10). This confirms that the conformational transition occurs, and low molecular weight CMC or CMC hydrolysate becomes significantly more stiff compared with higher molecular weight CMC. As shown repeatedly, ordinary CMC follows Gaussian chain distribution and behaves as a free draining random coil with Mark-Houwink exponents varying from 0.83–0.97. Upon hydrolysis, the low molecular weight CMC chain is no longer able to turn and the back bone forms a free strip, thereby relieving the intra-chain interactions (FIG. 6). Consequently, the conformation of the short chain corresponds to a rod-like shape with Mark-Houwink exponents varying from 1.2 to 2.0 and also results in the lower value of chain stiffness parameters. Experimental results (Table 5) show some deviation in the values of the chain stiffness parameter for higher molecular weight CMC. This may be due to the differences in the molecular weight distributions.

TABLE 4

The Chain Stiffness Parameter of CMC and CMC Hydrolysates

| CMC | Mw | Chain Stiffness Parameter (B) |
|---|---|---|
| Raw Materials | | |
| 7HFD | 687,500 | 0.014 |
| 7MFD | 292,700 | 0.015 |
| 7LFD | 108,600 | 0.018 |
| Finnfix 5E | 50,200 | 0.013 |
| Finnfix 2 Lot#59135 | 30,700 | 0.015 |
| Finnfix 2 Batch 59379-1 | 20,200 | 0.014 |
| Hydrolysates | | |
| 151.70 1 h | 14,400 | 0.019 |
| 1511 | 10,400 | 0.014 |
| 1512 | 9.400 | 0.011 |
| 151/63.1 hr. | — | 0.010 |
| 151/63.24 hrs | 6,500 | 0.008 |
| 151/47 | — | 0.005 |
| 151/46 | 5,800 | 0.006 |
| 1512 Fr.A | 6,000 | 0.003 |

Example 4: Preparation of a Starch Precursor Hydrolyzate

Starch derivative hydrolyzates may be prepared from starch derivatives as defined above by an enzymatic hydrolysis utilizing an amylolytic preparation having α-amylase as the main active hydrolytic agent such that the only insignificant amounts of mono- and disaccharides are produced. The hydrolysis procedure is generally carried out by dissolving the starch derivative in water, adjusting the pH and the temperature to the valve suitable for the enzyme activity, adding the enzyme activity, adding the enzyme to the solution and allowing the enzyme to react for a suitable time. After the enzyme reaction, the enzyme is inactivated by heating the solution up to about 100° C. and the hydrolyzate product is concentrated and dried. The average degree of polymerization (DP) of the polymers obtained by such a hydrolysis is less than 500. The specific conditions suitable for and the specific time sufficient to secure the desirable degree of hydrolysis may be readily determined for each selected starch derivative and each selected enzyme preparation.

Similarly, where degradation is carried out using chemical or physical means, the average DP of the oligomers produced is less than 500.

60 g of carboxymethyl starch (CM starch) derived from potato starch (Primojel; Avebe, 9607 PT Foxhol, The Netherlands) was mixed in 1200 ml of water. The temperature of the mixture was raised to 80° C. and the suspension was mixed continuously. About 1.5 ml of amylase (Ban 120L, Novo, Industri A/S, Novo Alle, 2880 Bagsvaerd, Denmark) diluted 1/50 by volume was added to the suspension mixture. After hydrolysis of about 30 minutes the enzyme was inactivated by heating (100° C., 10 min.). The hydrolyzate was then freeze-dried.

The hydrolyzate had an average DP of about 350 as estimated from end group analysis (reducing sugar measurement) and contained negligible amounts of glucose, maltose and oligosaccharides, as the value of reducing sugars was 0.28%. The viscosity of a 5% by weight suspension of the hydrolyzate, measured using Haake-Rotovisco RV 12 viscometer with sensor systems NV; Karlsruhe, Federal Republic of Germany at 25° C. was 57 mPa.s using the shear rate of 692 l/s. The viscosity of the unhydrolyzed raw CM starch material was 106 mPa.s (25° C., 692 l/s). Since the viscosity of the hydrolysates is much lower, the hydrolysates can be used at much higher concentrations than the original high molecular weight starch derivatives.

Example 5: Preparation of Capsules Using Carboxymethyl Cellulose Hydrolyzates (a) One hundred ml of 4 percent (w/v) gelatin from porcine skin (bloom strength 175) was dissolved in distilled water and 100 ml of 1 percent (w/v) carboxymethyl cellulose hydrolyzate having an intrinsic viscosity of 31.4 ml/g (average DP about 50) was prepared in distilled water at 60° C. The CMC hydrolyzate solution and gelatin solution were placed in a 1000 ml beaker, mixed, and the pH of the solution adjusted to 10. One hundred and fifty ml of soybean oil was added to the solution while stirring with a magnetic stirrer at 100 rpm. After forming a stable emulsion, the pH was adjusted to 4 to provide conditions for electrostatic interaction to take place between gelatin and CMC hydrolyzate.

The temperature of said solution was decreased to less than 15° C. for the gelation of gelatin on the surface of the coacervated capsules. The capsules were washed with water to remove residual gelatin. Spherical capsules were formed with sizes ranging from 400μ to 500μ.

Figure 2:
FIG. 2 is a photomicrograph of capsules formed using CMC hydrolyzates.

Capsules were then suspended in 1 percent glutaraldehyde solution and stirred for 15 minutes to strengthen the capsule walls. Capsules were washed with water and the water was decanted by using a strainer. A capsule slurry was obtained and some portion of the capsule slurry was dried. The capsules have a thin membrane with wall thickness less than about 2μ (FIG. 2).

Figure 3:
FIG. 3 is a photomicrograph of capsules formed using high molecular weight CMC.

(b) Capsules were prepared with the same procedure as above but with high molecular weight CMC having an intrinsic viscosity of 280.4 ml/g (the average DP about 700) instead of CMC hydrolyzate. These capsules had a membrane with thickness more than 10μ and had irregularities on the membrane walls (FIG. 3).

Capsules obtained in each example were subjected to the following tests:

Sonication Test

To test for relative strength, the capsules were sonicated. Six ml of water and 0.1 ml of fully hydrated capsule slurry was mixed. After standing for 5 minutes, capsules were sonicated using Bransonic Ultrasonic cleaner Model 1200 (Danbury, Conn.) for 2 minutes. Ultrasonic treatment breaks the capsules and then releases the oil. The oil released is indicated by increased turbidity in the aqueous phase. The turbidity of the aqueous phase was measured by a spectrohotometer at 595 nm. Higher turbidity indicates more broken capsules, therefore, more fragile and unstable capsule membranes.

Heating Test

This test provides relative values on the thermal stability and mechanical strength of the capsules. Known amount of capsules were spread on glass microscope slides and dried in a 50° C. oven overnight. Then the sample was heated at 265° C. for 20 minutes. The amount of oil loss was measured.

Suspended Volume Measurement

In order to measure the total volume of the capsules, prepared capsules were suspended quantitatively in 1000 ml of water. The volume of the capsules suspended was determined in a graduated cylinder.

Results

Capsules prepared from carboxymethyl cellulose hydrolyzates (CMC hydrolyzates) had an absorbance of 0.86 at 595 nm in the sonication test. Five percent of oil was lost as determined by the baking test, and the suspended volume was 217 ml. However, the capsules prepared using high molecular weight carboxymethyl cellulose had an absorbance of 1.30. Nine percent of oil was lost according to the baking test, and the suspended volume was 280 ml.

According to these tests, capsules prepared with low molecular weight hydrolyzates are more stable, have a stronger capsular membrane, occupy less volume and are more compact than capsules prepared with high molecular CMC. Therefore, capsules prepared with CMC hydrolyzate can contain more oil within a given volume with superior mechanical properties.

(c) Carboxymethyl cellulose hydrolyzate capsules were prepared as described in 5(a) together with 200 ml of oil.

(d) High molecular weight carboxymethyl cellulose capsules were prepared as described in 5(b) together with 200 ml of oil.

Test results indicate that capsules prepared with CMC hydrolyzate have thinner membranes and better mechanical properties than capsules prepared with high molecular weight CMC.

(e) Carboxymethyl cellulose hydrolyzate capsules were prepared as described in 5(a) together with 250 ml of oil.

(f) High molecular weight carboxymethyl cellulose capsules were prepared as described in 5(a) together with 250 ml of oil.

Capsules prepared with CMC hydrolyzate had a thin membrane and spherical shape with no leaking or rupturing of the capsules. However, the capsules prepared with high molecular weight CMC leak a considerable amount of oil with breaking of many capsules, probably due to lack of mechanical strength of the capsular membrane.

(g) CMC hydrolyzate having an intrinsic viscosity of 18.6 ml/g, (the average DP about 20) were used to prepare the capsules in the same general manner described in 5(a).

(h) CMC hydrolyzate capsules were prepared with gelatin having a bloom strength of 300.

(i) CMC hydrolyzate capsules were prepared with two percent gelatin having a bloom strength of 175 in the same general manner described in 5(a).

(j) High molecular weight CMC capsules were prepared with two percent gelatin having a bloom strength of 175 in the same general manner described in 5(b).

Test results indicate that the capsules prepared using carboxymethyl cellulose hydrolyzates are superior in mechanical property to those prepared with high molecular weight CM cellulose.

Example 6: Preparation of Capsules Using Carboxymethyl Starch Hydrolyzates

The same general procedures of Example 5 was repeated with carboxymethyl starch hydrolyzate and with carboxymethyl (CM) starch of higher molecular weight (Primojel: Avebe, 9607 PT Foxhol, The Netherlands). The carboxymethyl starch hydrolyzate was prepared as described in Example 4, having an average DP of about 350.

(a) Capsules were prepared using Carboxymethyl (CM) starch hydrolyzate.

(b) Capsules were prepared using high molecular weight Carboxymethyl starch.

Figure 4:
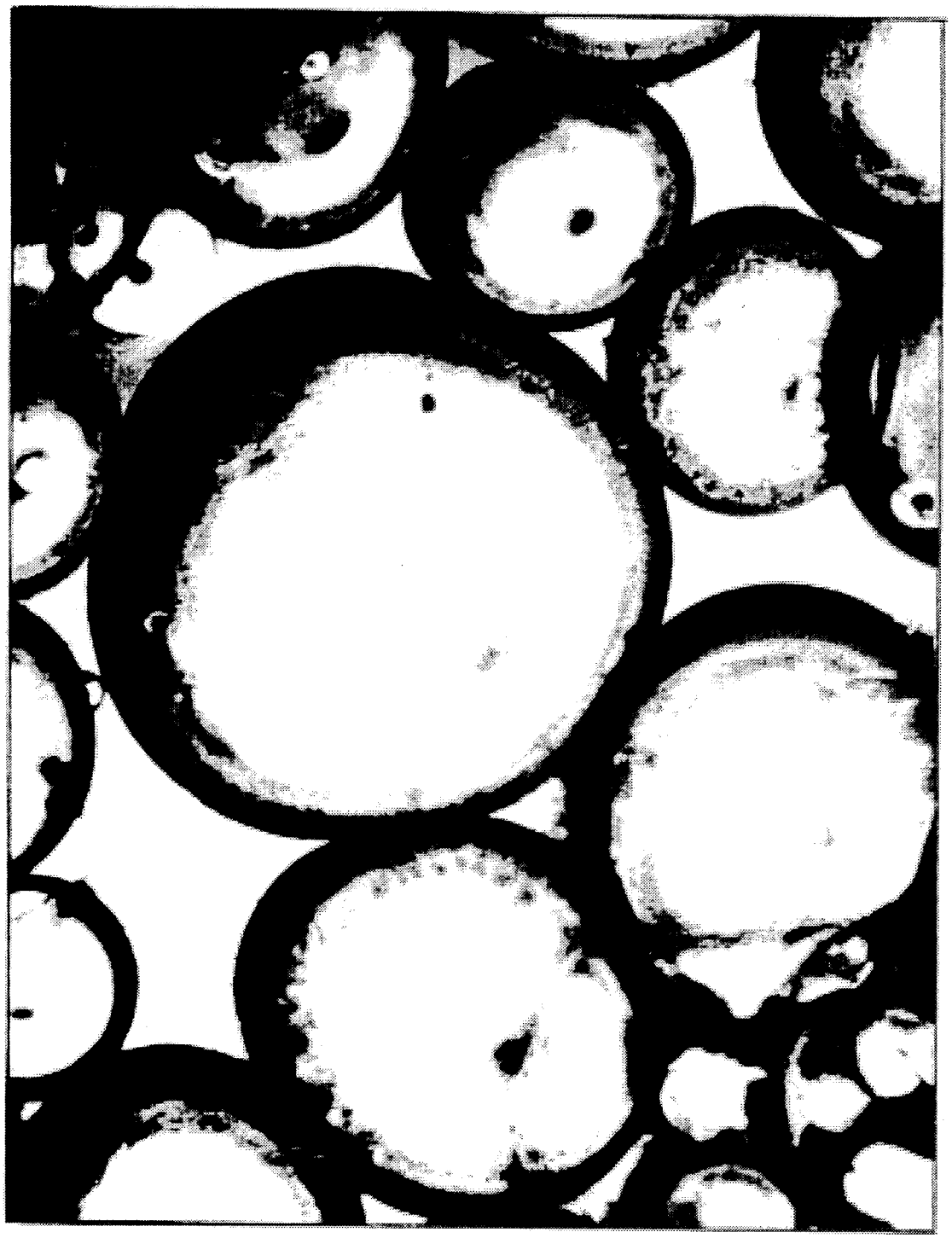
FIG. 4 is a photomicrograph of capsules formed using CM Starch hydrolyzates.
Figure 5:
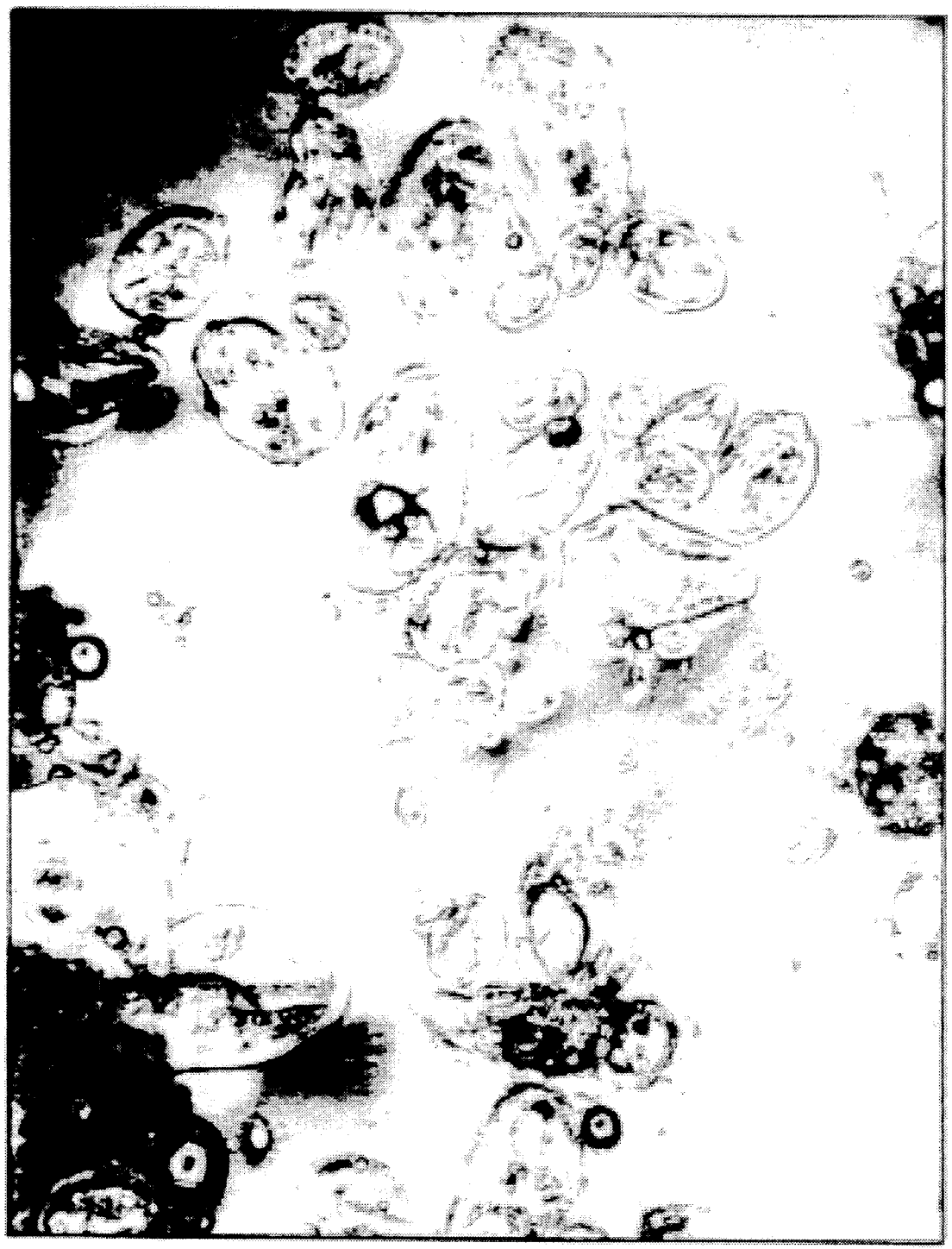
FIG. 5 is a photomicrograph of capsules formed using CM Starch.

Capsules prepared using the carboxymethyl starch hydrolyzate had a fairly spherical shape of about 300µ diameter with thin membrane (FIG. 4). However, the capsules prepared using carboxymethyl starch were mostly broken (FIG. 5).

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. An insoluble polymeric capsule comprising at least two polymeric components, wherein one of said components is a hydrophilic colloid, and another of said components comprises an enzymatically degraded product of a cellulose derivative, the degraded product consisting essentially of a mixture of oligomers, a majority of said oligomers having a degree of polymerization between about 5 and about 50.

2. The capsule of claim 1, further comprising a selected substance encapsulated within the capsule.

3. The capsule of claim 1, wherein the hydrophilic colloid is a gellable material selected from the group consisting of gelatin, albumin, gum arabic, alginates, casein, agar, and pectins.

4. The capsule of claim 1 wherein the mixture of oligomers have molecular weights such that the polydispersity index of the mixture is less than about two.

5. The capsule of claim 1 wherein the degraded product contains less than about 25% by weight of monosaccharides, disaccharides or mixtures thereof.

6. The capsule of claim 5 wherein the degraded product contains less than about 10% by weight of monosaccharides, disaccharides or mixtures thereof.

7. The capsule of claim 1 wherein the cellulose derivative is carboxymethyl cellulose.

8. The capsule of claim 1 wherein the mixture of oligomers has an average molecular weight of less than about 15,000 daltons.

9. An insoluble polymeric capsule comprising at least two polymeric components, wherein one of said components is a hydrophilic colloid, and another of said components comprises an enzymatically degraded product of a cellulose derivative, the degraded product consisting essentially of a mixture of oligomers, a majority of said oligomers having a Mark-Houwink exponent of at least 1.2 at an NaCl concentration of 0.005N to 0.5N, wherein said cellulose derivative has at least one substituent selected from the group consisting of carboxymethyl, methyl, hydroxyethyl, hydroxymethylethyl, hydroxypropylmethyl and hydroxypropylethyl.

10. The capsule of claim 9 wherein the degraded product consists essentially of the mixture of polymers.

11. The capsule of claim 9, further comprising a selected substance encapsulated within the capsule.

12. The capsule of claim 9 wherein the hydrophilic colloid is a gellable material selected from the group consisting of gelatin, albumin, gum arabic, alginates, casein, agar, and pectins.

13. The capsule of claim 9 wherein the mixture of oligomers have molecular weights such that the polydispersity index of the mixture is less than about two.

14. The capsule of claim 9 wherein the degraded product contains less than about 25% by weight of monosaccharides, disaccharides or mixtures thereof.

15. The capsule of claim 14 wherein the degraded product contains less than about 10% by weight of monosaccharides, disaccharides or mixtures thereof.

16. The capsule of claim 9 wherein the cellulose derivative is carboxymethyl cellulose.

17. The capsule of claim 1 wherein the mixture oligomers has an average molecular weight of less than about 15,000 daltons.

18. A method for making polymeric capsules comprising:
(a) selecting a derivative of cellulose for degradation into a mixture of oligomers,
(b) enzymatically degrading the selected cellulose derivative into a mixture of oligomers, a majority of which have a degree of polymerization between about 5 and about 50;
(c) combining the mixture of oligomers and a polymeric hydrophilic colloid in aqueous solutions;
(d) subjecting the combination to conditions such that the colloid and the oligomers interact to form polymeric capsules.

19. The method of claim 18 further comprising admixing the combination with a substance to be encapsulated thereby forming capsules containing the substance.

20. The method of claim 18 wherein the cellulose derivative has at least one substituent selected from the group consisting of carboxymethyl, methyl, hydroxypropyl, methylethyl, hydroxyethyl, hydroxyemethylethyl, and hydroxypropylmethyl.

21. The method of claim 18 further comprising strengthening the insoluble polymeric capsules by cross linking the membrane with a cross-linking agent.

22. The method of claim 19 wherein the substance is selected from the group consisting of oil, oil-phases, and bioactive substances.

23. The method of claim 19 wherein the substance is selected from the group consisting of cosmetics, food compositions, feed compositions and pharmaceuticals.

24. The method of claim 18 wherein the mixture of oligomers have molecular weights such that the polydispersity index of the mixture is less than about two.

25. The method of claim 18 wherein the mixture of oligomers contains less than about 25% by weight of monosaccharides, disaccharides or mixtures thereof.

26. The method of claim 18 wherein the mixture of oligomers contains less than about 10% by weight of monosaccharides, disaccharides or mixtures thereof.

27. The method of claim 20 wherein the mixture of oligomers has an average molecular weight of less than about 15,000 daltons.

28. The method of claim 18 wherein the mixture of oligomers has an average molecular weight of less than about 15,000.

29. A method for making polymeric capsules comprising:
   (a) selecting a derivative of cellulose for degradation into a mixture of oligomers;
   (b) degrading the selected cellulose derivative into a mixture of oligomers, the majority of which have a Mark-Houwink exponent of at least about 1.2 at an NaCl concentration of 0.005N to 0.5N;
   (c) combining the mixture of oligomers and a polymeric hydrophilic colloid in aqueous solution;
   (d) subjecting the combination to conditions such that the oligomers and the colloid interact to form polymeric capsules.

30. A method of making oil containing capsules comprising the steps of:
   (a) selecting an oil to be encapsulated;
   (b) selecting a derivative of cellulose for degradation into a mixture of oligomers;
   (c) degrading the selected cellulose derivative into a mixture of oligomers having a selected charge and a degree of polymerization such that a majority of the oligomers conforms to a rod-like configuration and have a degree of polymerization between about 5 and about 50;
   (d) selecting a polymeric hydrophilic colloid having a charge opposite to the charge of the oligomers;
   (e) admixing the oil, the mixture of oligomers and the hydrophilic colloid in aqueous solution;
   (f) adjusting the pH of the solution such that the oligomers and the hydrophilic colloid interact to form capsules, the oil being encapsulated upon formation of the capsules.

31. A method of preparing a foodstuff for consumption comprising:
   (a) selecting a foodstuff;
   (b) admixing with the selected foodstuff, capsules according to claim 2 or 11 which contain an edible oil as the encapsulated substance;
   (c) subjecting the mixture of the foodstuff and capsules to conditions such that the capsules release the encapsulated oil onto the selected foodstuff.

32. A food composition comprising a selected foodstuff and a plurality of capsules according to claim 2 or 11 the capsules containing an edible oil as the encapsulated substance and being rupturable upon exposure to a selected temperature.

* * * * *